United States Patent
Hursey, Jr.

(10) Patent No.: US 6,604,823 B2
(45) Date of Patent: Aug. 12, 2003

(54) MAGNIFYING SAFETY GLASSES

(76) Inventor: Archibald Wesley Hursey, Jr., 810 Indigo Ct., Mt. Pleasant, SC (US) 29464

( * ) Notice: Subject to any disclaimer, the term of this patent is extended or adjusted under 35 U.S.C. 154(b) by 0 days.

(21) Appl. No.: 09/927,998

(22) Filed: Aug. 10, 2001

(65) Prior Publication Data

US 2003/0030771 A1 Feb. 13, 2003

(51) Int. Cl.[7] ................................................. G02C 7/02
(52) U.S. Cl. ........................... 351/61; 351/44; 351/123; 351/157
(58) Field of Search ............................... 351/41, 44, 54, 351/168, 169, 170, 171, 172, 123, 61, 156, 157, 158, 62

(56) References Cited

U.S. PATENT DOCUMENTS

| | | | |
|---|---|---|---|
| 4,563,065 A | | 1/1986 | Kreissl |
| 4,796,986 A | | 1/1989 | Gowdy, Jr. |
| 4,810,080 A | | 3/1989 | Grendol et al. |
| 5,153,619 A | | 10/1992 | Nix |
| 5,170,502 A | | 12/1992 | Hegendorfer et al. |
| 5,475,449 A | * | 12/1995 | Pyle ............................ 351/123 |
| 5,493,348 A | | 2/1996 | Herald, Jr. et al. |
| 5,541,677 A | * | 7/1996 | Huhtala ....................... 351/156 |
| 5,786,882 A | * | 7/1998 | Satterthwaite .............. 351/156 |
| 5,790,230 A | | 8/1998 | Sved |
| 5,805,258 A | | 9/1998 | Wiedner |
| 6,196,678 B1 | * | 3/2001 | Chapin, III ................... 351/44 |
| 6,231,178 B1 | * | 5/2001 | Greaves ........................ 351/44 |

OTHER PUBLICATIONS

Duluth Trading Company, Late Summer 2001, p. 37, vol. T21, Issue No. 6, Duluth Trading Company 170 Countryside Drive, P.O. Box 409, Belleville, WI 53508.

* cited by examiner

*Primary Examiner*—Huy Mai
(74) *Attorney, Agent, or Firm*—Kathleen M. Harleston; Harleston Law Firm, LLC

(57) ABSTRACT

A magnifying safety glasses assembly (10) for use by persons with presbyopia, the assembly (10) including a front safety eyepiece portion (11) made substantially of a transparent, nonmagnifying, shatter-proof material, and matching right and left temple portions (12), each affixed to an end of the front eyepiece portion (11), wherein the front safety eyepiece portion includes at least one built-in magnifying corrective segment (13) for correction of a user's near vision. The safety glasses assembly (10) preferably also includes a retainer strap (16) and earplugs (17), each earplug (17) being attached to an end of the retainer strap (16).

15 Claims, 3 Drawing Sheets

MAGNIFYING SAFETY GLASSES

BACKGROUND OF THE INVENTION

1. Technical Field

The present invention relates to a safety glasses assembly incorporating built-in magnifying segments, and preferably a retainer strap and earplugs.

2. Background Information

Safety glasses are well known and commonly available to protect the eyes during work with certain equipment and tools from sparks, flying objects, and particles, and other activities that may pose a threat to the eyes. Various types of earplugs are commonly used to protect the ears from loud noises associated with certain equipment, especially power tools.

Many users of safety glasses have presbyopia, a condition of the eye that afflicts most adults past the age of forty. Presbyopia is a form of hyperopia, or farsightedness. In hyperopia, the eyeball is too short from front to back, which causes rays of light entering the eye to be brought to a focus behind the retina. This is in contrast with myopia, or nearsightedness. The myopic person's eyeballs are too long from front to back, causing rays of light to be brought into focus in front of the retina. Myopia can also be caused by the media of the eye having increased strength in refractive power. Presbyopia is caused by the loss of elasticity of the crystalline lens as a result of advancing age. This causes the near point of distinct vision to be removed farther from the eye. People with presbyopia commonly wear corrective lenses in the form of inexpensive reading glasses, which can be found in many drug stores and purchased without a prescription, or bifocals, which require a prescription, for near vision.

Many older Americans have jobs or hobbies which require that safety glasses be worn. When using safety glasses, the presbyopic wearer often needs to use near vision, but cannot conveniently and effectively wear corrective lenses with the safety glasses. Wearing two pairs of glasses, one pair of reading glasses under one pair of safety glasses, is uncomfortable and cumbersome. To have safety glasses made with prescription lenses would be prohibitively expensive for most people. There is a need for a simple way to allow a wearer the benefit of both safety glasses and simple inexpensive reading glasses at the same time, without the discomfort of attempting to wear two pairs of glasses together.

Existing inventions include lenses that can be attached or mounted to the frames of safety glasses. These are cumbersome and do not address the situation of an individual who has presbyopia and needs magnification for near vision, but does not need prescription lenses for other types of vision impairment. That individual can easily purchase inexpensive reading glasses for ordinary use, choosing from among several standard magnifications without a prescription. With the present invention, the same individual could purchase inexpensive safety glasses with the same benefit, because the present invention can be manufactured with built-in corrective segments in a number of standard magnifications. Furthermore, magnifying safety glasses according to the present invention can be sold without a prescription and therefore do not require the inconvenience and expense of periodic trips to an ophthalmologist, optometrist, or other eyecare specialist.

The present invention can also be manufactured with a retaining strap, so the user can sling the glasses around her neck when they are not in use, and earplugs, which she can wear during exposure to noise. With the retaining strap, the wearer can remove the earplugs without losing them, and can conveniently keep them with the safety glasses, where they are most apt to be needed. The wearer need not search around the house or workplace for three separate items: reading glasses, safety glasses, and earplugs.

BRIEF SUMMARY OF THE INVENTION

The present invention is a magnifying safety glasses assembly for use by persons with presbyopia, generally comprising a front safety eyepiece portion made substantially of a transparent, nonmagnifying, shatter-proof material, and matching right and left temple portions, each affixed to an end of the front eyepiece portion. The front eyepiece portion comprises at least one built-in magnifying corrective segment for correction of a user's near vision. In a preferred embodiment, the safety glasses also include a retaining strap by means of which a pair of earplugs can be attached to and made a part of the safety glasses assembly.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
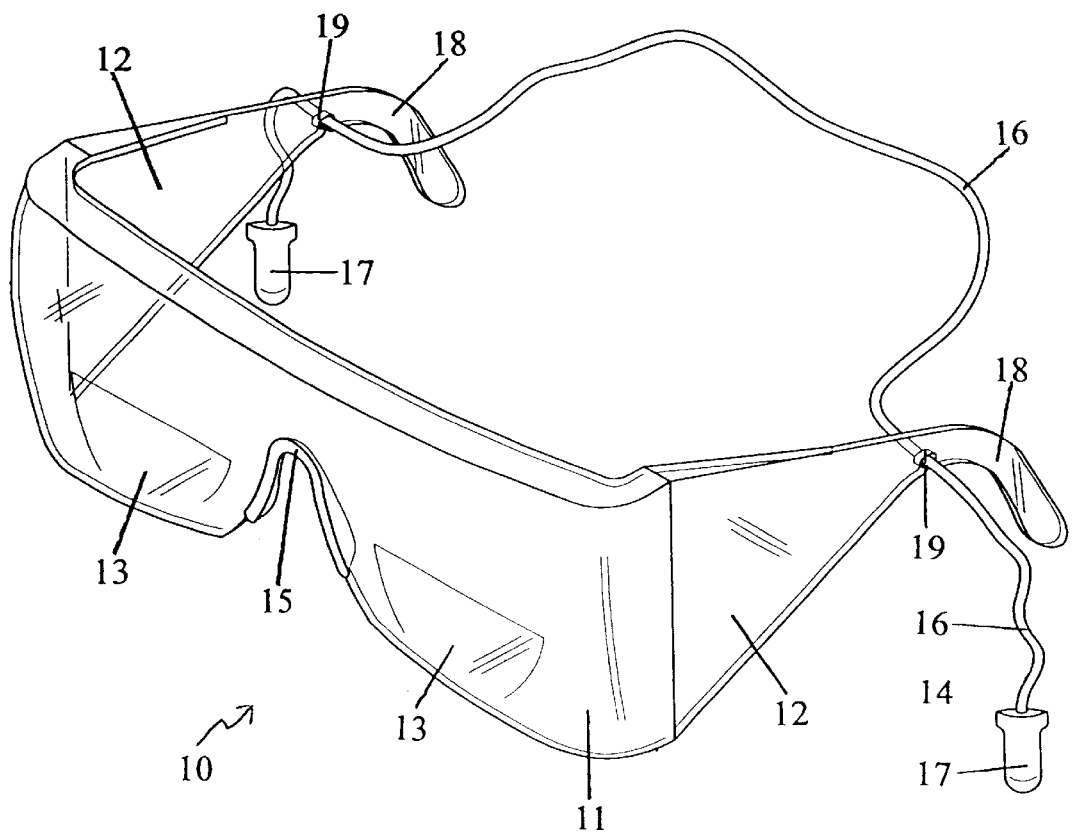
FIG. 1 is a front perspective view of a safety glasses assembly according to the present invention.

In the following description, like reference characters designate like or corresponding parts throughout the several views. Also, in the following description, it is to be understood that such terms as "front," "back," "bottom," and the like are words of convenience and are not to be construed as limiting terms. Referring in more detail to the drawings, the invention will now be described.

Figure 2:
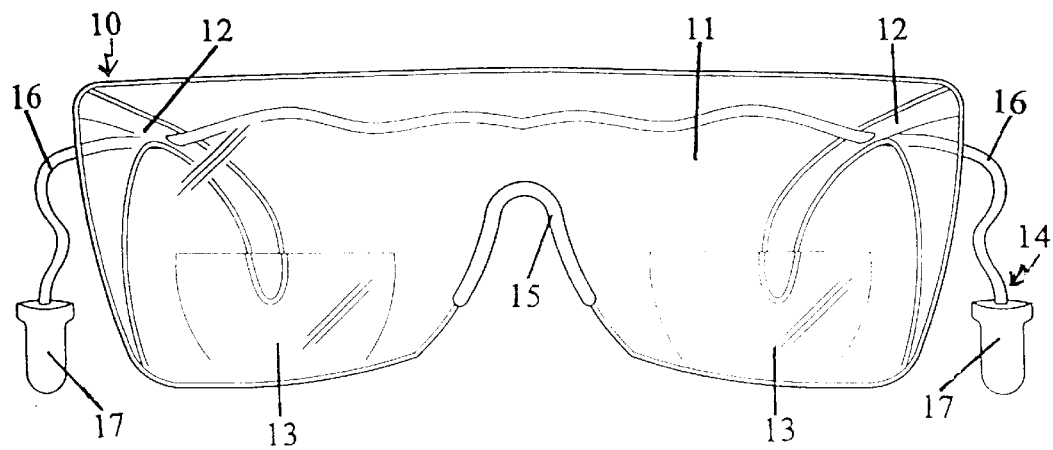
FIG. 2 is a front elevational view of the safety glasses assembly according to FIG.

Turning to FIG. 1 and FIG. 2, a magnifying safety glasses assembly, generally referred to as 10, for use by older people with presbyopia, generally comprises: a front safety eyepiece portion 11 made substantially of a transparent, nonmagnifying, shatter-proof material, and matching right and left temple portions 12, each temple portion being affixed to an opposite end of the front eyepiece portion 11. The front eyepiece portion 11 comprises at least one built-in magnifying corrective segment 13 for correction of a user's near vision. In the preferred embodiment shown in FIG. 1 and FIG. 2, the front safety eyepiece portion 11 comprises two of the built-in magnification segments 13, with one magnification segment 13 on a lower half of each side of the front eyepiece portion 11. The front safety eyepiece portion preferably comprises a nose-piece 15 extending laterally backwards from the lower center of the front eyepiece portion 11. Preferably, one magnification segment is built into each side of the front safety eyepiece portion 11 on either side of the nose-piece 15. The safety glasses assembly 10 preferably further comprises an earplug/retainer strap portion 14.

In the preferred embodiment shown in FIGS. 1 and 2, the front eyepiece portion 11, and the right and left temple portions 12, are molded, unitary, transparent pieces made of a plastic material. The front eyepiece portion 11 is preferably of a nonmagnifying, shatter-proof plastic, except for the left and right magnification segments 13. Each magnification segment 13 is of a generally half moon or semicircular shape, positioned such that the arc of the segment is oriented downward and the top of the segment is a straight edge. The straight edge preferably extends across a central part of the lower portion of the front eyepiece portion, so that the magnification segments 13 are in front of the wearer casting a downward gaze. Each magnification segment 13 is constructed with a curvature that provides a predetermined desired magnification. The front eyepiece portion 11 is preferably made to ANSI (American National Standards Institute) standards.

The safety glasses assembly 10 can be manufactured with magnification segments 13 in a variety of common magnification strengths, according to the needs of different wearers. Preferably, the magnifying segment has a magnification value of between 1 and 4 diopters, in increments of 0.25. A diopter is a unit of refractive power of lenses. The refractive power in diopters is the reciprocal of the focal length in meters. The magnifying segment herein most preferably has a magnification value of 1.25, 1.5, 1.75, 2, 2.25, 2.5, 2.75, or 3.

As shown in FIGS. 1 and 2, the generally rectangular, slightly convex front eyepiece portion 11 is indented at the approximate center of its lower longitudinal side, so that it sits properly on the bridge of the user's nose. The nose-piece 15 is preferably incorporated into or formed by the indentation. The bottom portion of the nose-piece is optionally padded.

Figure 3:
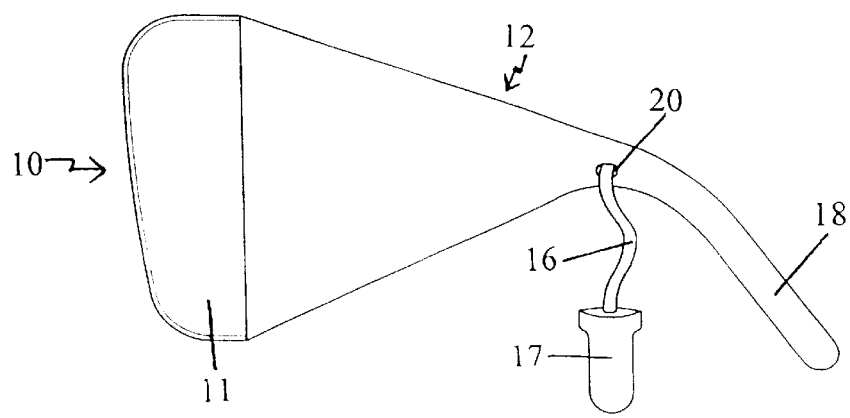
FIG. 3 is a left side elevational view of a safety glasses assembly according to the present invention.

Referring to FIG. 1, FIG. 2, and FIG. 3, preferred embodiments of the safety glasses assembly 10 include an earplug/retainer strap assembly 14, which includes a flexible retainer strap 16 and a set of earplugs 17. The earplugs are preferably lightweight, comfortable, and identical to one another. They are preferably made of a durable material that conforms to the shape of the Eustachian tube. The retainer strap is preferably made of a fabric, thin tubing, or a rubber-like material. In this preferred embodiment, the retainer strap 16 extends from one temple portion 12 to the other 12, preferably between curved temple bows 18 at a posterior end of each temple portion 12. The temple bows are the part of the glasses that is placed over the top of the ears when a user puts on the pair of glasses.

Each end of the retainer strap 16 is attached to one end of one of the earplugs 17, by adhesive means, for example, or by molding a polyurethane earplug around the end of the retainer strap. The wearer can use the earplugs as desired to protect her hearing from loud equipment or machinery or other excessive or repetitive noises. Alternatively, the earplugs 17 can dangle unused while the wearer is wearing the safety glasses 10. Or the earplugs can be used while the safety glasses rest on the wearer's chest or collarbone area.

Figure 4:
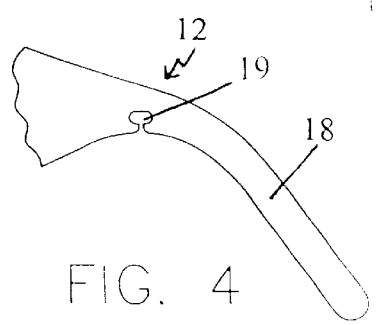
FIG. 4 is a left elevational view of a posterior portion of an eyeglass temple of the safety glasses assembly according to FIG. 1, showing a retaining strap notch.

Referring to FIG. 1 and FIG. 4, a preferred embodiment of the magnifying safety glasses 10 comprises a retainer strap notch 19 in each temple portion 12, preferably at the approximate anterior end of the temple bow 13. The notch 19 is preferably generally balloon-shaped and formed into the plastic, the narrow opening on the lower edge of the temple portion 12 being sized just wide enough to allow passage of the retainer strap 16 into the wider interior portion of the notch 19, allowing the wearer to remove the earplug/retainer strap assembly 14 when desired, but making it difficult for the retainer strap 16 to become accidentally dislodged and the earplug/strap assembly 14 to fall off. In FIG. 1 and FIG. 4, the retainer strap notch 19 is shown on the bottom edge of the temple portion 12, so that the retainer strap 16 is snapped into place from below; the notch 19 could also be placed along the upper edge of the temple portion 12 with equal effect.

Figure 5:
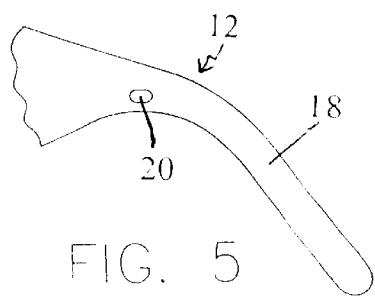
FIG. 5 is a left elevational view of a posterior portion of an eyeglass temple of the safety glasses assembly according to FIG. 3, showing a retaining strap hole.

Turning to FIG. 3 and FIG. 5, in an alternate embodiment, a circular or elliptical-shaped retainer strap hole 20 is located on each temple portion 12, instead of the notch 19, but in the same position as the notch 19. The earplugs prevent the retainer strap from backing out through the hole or notch. The retainer strap 16 can be threaded through the retainer strap hole 20 during manufacture and remain permanently attached to the assembly 10, or the earplugs 17 may be made so that they can be removed from the retainer strap 16, in which case the earplug/retainer strap assembly 14 could be removed by first removing one earplug 17 from the retainer strap 16 and then unthreading the retainer strap 16 through the retainer strap hole 20. Other means of attaching the retainer strap 16 to the glasses assembly 10, such as threading it through an eye on the outside of each temple portion 12, may also be employed herein.

The retainer strap 16 is preferably long enough, most preferably between about 20 and 40 inches in length, for the wearer to put the safety glasses assembly 10 on by slipping his head through the strap. The retainer strap 16 can then be left loose, or it can be tightened around the user's neck by pulling one end or both ends of the retainer strap 16. When they are not in use, the wearer can take off the safety glasses assembly 10 and leave it hanging in front of him, with the retaining strap around the back of his neck.

To use the earplugs 17, the user slides the ends of the retainer strap 16 through the retainer strap hole 20 or notch 19 until it is long enough for the earplug 17 to reach the user's ear canal. The user then places the earplug in the ear canal. After use, the user can remove the earplugs 17 by pulling the portion of the retainer strap 16 nearest the ear.

Advantages of the present invention include protection of the wearer's eyes during work with tools and equipment or other activity that pose a threat to the wearer's eyes, without compromising visibility. The magnification allows the user to read small print, see small parts of equipment, assess the job she has done, etc., without being inconvenienced. Since the magnification segment 13 only extends over a portion of the lens, with the curved side edges and the straight upper edges of each magnification segment not extending to the nose-piece or the side edges of the front eyepiece portion (see FIGS. 1, 2 and 6), the user's vision is enhanced and not impaired. The user can chose a level of magnification appropriate to his level of vision impairment when he purchases the safety glasses assembly 10.

The magnifying safety glasses assembly 10 also allows the wearer to protect his or her hearing without additional devices, and combines hearing protection with a simple and effective means to retain both the safety glasses assembly and the earplugs when not in use. The user need not search for his safety glasses or tiny earplugs each time he lifts up the blowtorch, etc., because they are dangling around his neck on the retainer strap 16. The safety glasses assembly 10 is also convenient in that the user need not search for three pieces: safety glasses, earplugs, and a retainer strap, before undertaking a task requiring eye/ear protection. The retainer strap 16 also provides a means of pulling out the earplugs 17 once the task is complete.

In short, a preferred safety glasses assembly herein comprises:
  a) a one-piece front safety eyepiece portion made substantially of a transparent, nonmagnifying, thermoplastic base material, the front safety eyepiece portion comprising a central indentation on its lower side for accommodating the user's nose;
  b) two matching built-in magnifying corrective segments for correction of a user's near vision, with one magnification segment on each side of the front eyepiece portion;
  c) matching right and left temple portions, each affixed at an anterior end to a corresponding end of the front safety eyepiece portion;
  d) a flexible retainer strap connecting the two temple portions; and
  e) two earplugs, each being affixed to one end of the retainer strap.

The one-piece front safety eyepiece portion 11 is preferably injection molded of a thermoplastic material, most preferably a thermoplastic polyurethane or thermoplastic elastomer material. The surface of the front eyepiece portion 11 can be coated with a suitable coating for blocking harmful ultraviolet rays from the sun or an industrial process, or for hunting, etc. The temple portions 12 preferably each have a temple bow area 18 at their posterior ends. The flexible retainer strap 16 connects the two temple bows 18, and each temple bow comprising a matching retainer strap hole 20 or generally balloon-shaped notch 19 through which one end of the retainer strap 16 slidably extends. The two holes or notches are preferably identical to one another. The anterior end 24 of each temple portion 12 is hinged to the corresponding end of the front eyepiece portion 11. The earplug and retainer strap are preferably removable.

Figure 6:
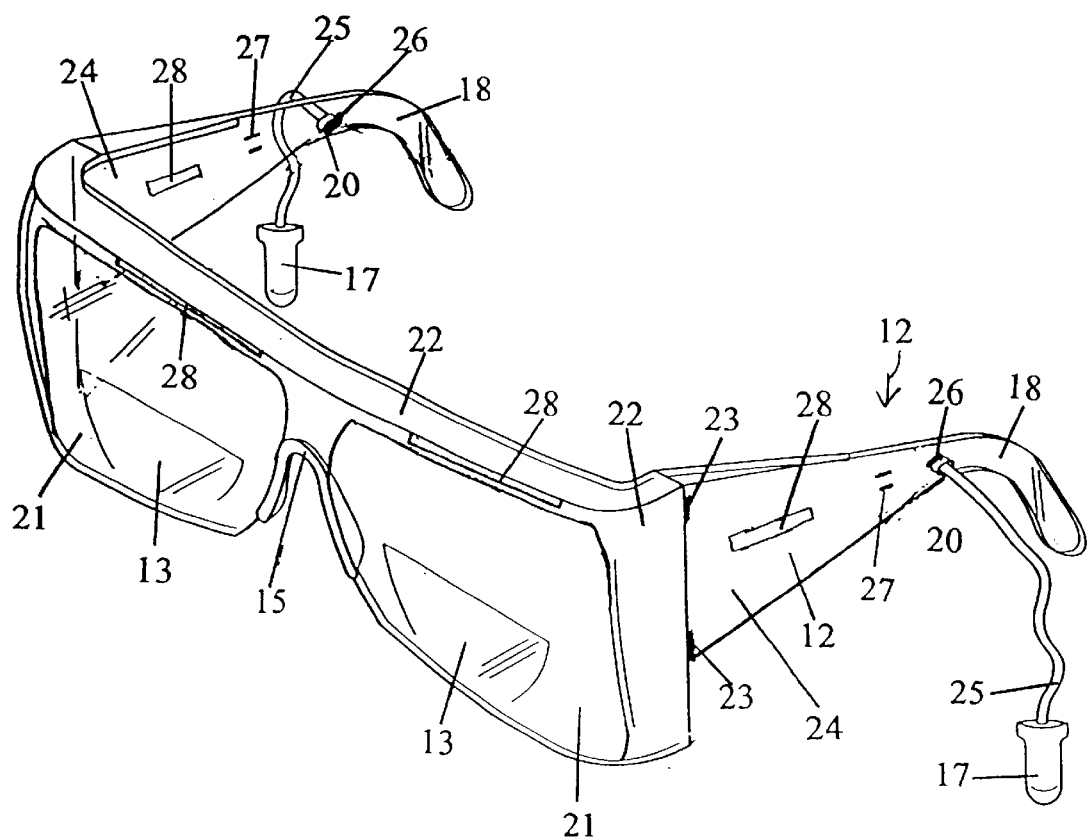
FIG. 6 is a front perspective view of an alternate embodiment of a safety glasses assembly according to the present invention.

As shown in the alternate embodiment illustrated in FIG. 6, the front eyepiece portion 11 comprises one, or two matching, lenses 21 surrounded by a frame 22, each lens 21 comprising the built-in magnification segment 13. The lenses 21 are set into the frame 22 by conventional means, such as a suitable adhesive.

In the preferred embodiments of FIG. 1 and FIG. 6, each temple portion 12 has one or two eyeglass hinges 23 attaching it to the front eyepiece portion 11. The two portions of each hinge 23 attach to the end of the front eyepiece portion 11 and to an anterior end 24 of each temple portion 12. Each temple portion, then, is hinged at its anterior end 24 to a corresponding end of the front eyepiece portion 11 (e.g., the left temple portion 12 is hinged to the left end of the front eyepiece portion 11).

Continuing with the alternate embodiment of FIG. 6, the lightweight earplugs 17 are attached directly to the temple portions 12 by means of a short earplug tether 25. The upper end of each tether 25 is attached to the temple portion 12 by adhesive, for example, or by passing the end of the tether 25 through a hole in the temple bow 18 and knotting or fusing the end of the tether. A knot 26 at the end of the tether 25 is shown in FIG. 6. The earplugs can be inserted in the ear canals, or dangle freely next to the ears when unused. The safety glass assembly 10 further comprises a small earplug clasp 27, which is attached to the outside of each temple portion 12 within reach of the earplug tether. When the earplug 17 is not in use, the user has the option of placing it in the clasp 27 for storage. The earplug clasp 27 has the added advantage of keeping the earplugs 17 relatively clean during storage of the safety glasses assembly 10.

Since safety glasses generally block ventilation around the eye area, the wearer may perspire, causing the lenses to fog up. To remedy that, the anterior ends 23 of the temple portions 12 can be made narrower, as shown in FIG. 6, but that reduces the area of protection from peripheral flying objects. As illustrated in FIG. 6, the temple portions 12 and/or front eyepiece portion 11 optionally include vertical or horizontal air slots 28 or holes for venting air. The slots 28 are preferably slanted so that a small flying object striking the vent will not pass through to strike the wearer.

Also, the present invention could easily be adapted to other forms of safety glasses, for example, safety glasses consisting of one piece, with a front and two opposite temple pieces.

From the foregoing it can be realized that the described device of the present invention may be easily and conveniently utilized as a means for protecting the wearer's eyes and hearing during work with tools and equipment or other activity that pose a threat to the wearer's eyes or hearing. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Brief List of Reference Numbers Used in the Drawings 10 magnifying safety glasses assembly
11 front eyepiece portion
12 temple portions
13 magnification segments
14 earplug/retainer strap portion
15 nose-piece
16 retainer strap
17 earplugs
18 temple bow
19 retainer strap notch
20 retainer strap hole
21 lens
22 frame
23 hinges
24 anterior end of temple portion
25 earplug tether 26 tether knot
27 earplug clasp
28 air slots

What is claimed is:

1. A magnifying safety glasses assembly for use by persons with presbyopia, the assembly comprising:

a front safety eyepiece portion made substantially of a transparent, nonmagnifying, shatter-proof material, matching right and left temple portions, each affixed to an opposite end of the front eyepiece portion, and further comprising a pair of earplugs;

wherein the front safety eyepiece portion comprises at least one built-in magnifying corrective segment for correction of a user's near vision;

the front safety eyepiece portion comprises a nose-piece extending laterally backwards from the lower center of the front eyepiece portion, and two of the built-in magnification segments, with one magnification segment on each side of the front safety eyepiece portion on either side of the nose-piece; and the front safety eyepiece portion and the two temple portions are each injection molded from a thermoplastic base material to form a unitary construction.

2. A magnifying safety glasses assembly according to claim 1, further comprising a retainer strap extending between two earplugs, the retainer strap being connected to the safety glasses assembly, and each end of the retainer strap being attached to one of the earplugs.

3. A magnifying safety glasses assembly according to claim 1, wherein each earplug is attached to the safety glasses assembly by an earplug tether, one end of the tether being affixed to an earplug and an opposite end of the tether being affixed to a temple portion of the safety glasses assembly.

4. A magnifying safety glasses assembly according to claim 3, further comprising an earplug clasp attached to the outside of each temple portion for clasping the closest earplug tether.

5. A magnifying safety glasses assembly according to claim 4, wherein the magnifying segment has a magnification value of 1.25, 1.5, 1.75, 2, 2.25, 2.5, 2.75, or 3.

6. A magnifying safety glasses assembly according to claim 4, wherein each temple portion is hinged at an anterior end to a corresponding end of the front eyepiece portion.

7. A magnifying safety glasses assembly for use by persons with presbyopia, the assembly comprising:

a front safety eyepiece portion made substantially of a transparent, nonmagnifying, shatter-proof material, matching right and left temple portions, each a fixed to an opposite end of the front eyepiece portion;

wherein the front safety eyepiece portion comprises at least one built-in magnifying corrective segment for correction of a user's near vision; and wherein opposite ends of a retainer strap extend through opposite retainer strap notches in each temple portion.

8. A magnifying safety glasses assembly according to claim 7, wherein the front safety eyepiece portion comprises one, or two matching, lenses surrounded by a frame, each lens comprising the built-in magnification segment.

9. A magnifying safety glasses assembly for use by persons with presbyopia, the assembly comprising:

a front safety eyepiece portion made substantially of a transparent, nonmagnifying, shatter-proof material, and matching right and left temple portions, each affixed to an opposite end of the front eyepiece portion, and further comprising air slot in the front eyepiece portion or temple portions;

wherein the front safety eyepiece portion comprises at least one built-in magnifying corrective segment for correction of a user's near vision;

wherein the front safety eyepiece portion comprises a nose-piece extending laterally backwards from the lower center of the front eyepiece portion, and two of the built-in magnification segments, with one magnification segment on each side of the front safety eyepiece portion on either side of the nose-piece; and wherein the front safety eyepiece portion comprises one, or two matching, lenses surrounded by a frame, each lens comprising the built-in magnification segment.

10. A magnifying safety glasses assembly for use by persons with presbyopia, the assembly comprising:

a) a one-piece front safety eyepiece portion made substantially of a transparent, nonmagnifying, shatter-proof, thermoplastic base material, the front safety eyepiece portion comprising a central indentation on its lower side for accommodating the user's nose;

b) two matching built-in magnifying corrective segments for correction of a user's near vision, with one magnification segment on each side of the front eyepiece portion;

c) matching right and left temple portions, each affixed at an anterior end to a corresponding end of the front safety eyepiece portion;

d) a flexible retainer strap connecting the two temple portions; and e) two earplugs, each being affixed to one end of the retainer strap.

11. A magnifying safety glasses assembly according to claim 10, wherein the temple portions each have a temple bow area at their posterior ends, the flexible retainer strap connecting the two temple bows, each temple bow comprising a matching retainer strap hole through which one end of the retainer strap slidably extends.

12. A magnifying safety glasses assembly according to claim 10, wherein the temple portions each comprise a posterior temple bow area, each temple bow area comprising an identical, generally balloon-shaped notch through which one end of the retainer strap slidably extends.

13. A magnifying safety glasses assembly according to claim 12, wherein the anterior end of each temple portion is hinged to the corresponding end of the front eyepiece portion.

14. A magnifying safety glasses assembly according to claim 12, wherein the earplug and retainer strap are removable.

15. A magnifying safety glasses assembly according to claim 14, wherein the magnifying segments have a magnification value of between 1 and 4 diopters, in increments of 0.25.

* * * * *